US 8,062,888 B2

(12) United States Patent
Manuelidis

(10) Patent No.: US 8,062,888 B2
(45) Date of Patent: Nov. 22, 2011

(54) HIGH THROUGHPUT ASSAYS FOR TRANSMISSIBLE SPONGIFORM ENCEPHALOPATHIES (TSE)

(75) Inventor: Laura Manuelidis, New Haven, CT (US)

(73) Assignee: Laura Manuelidis, New Haven, CT (US)

( * ) Notice: Subject to any disclaimer, the term of this patent is extended or adjusted under 35 U.S.C. 154(b) by 1061 days.

(21) Appl. No.: 11/114,411

(22) Filed: Apr. 25, 2005

(65) Prior Publication Data

US 2010/0009436 A1      Jan. 14, 2010

Related U.S. Application Data

(60) Provisional application No. 60/564,748, filed on Apr. 23, 2004, provisional application No. 60/574,611, filed on May 25, 2004.

(51) Int. Cl.
G01N 33/68 (2006.01)
C12N 15/85 (2006.01)
C12N 7/00 (2006.01)

(52) U.S. Cl. .................. 435/373; 435/235.1; 435/325

(58) Field of Classification Search .................. None
See application file for complete search history.

(56) References Cited

FOREIGN PATENT DOCUMENTS

| | | |
|---|---|---|
| WO | WO-02/093164 | 11/2002 |
| WO | WO-03/001211 | 1/2003 |
| WO | WO-03/081249 | 10/2003 |

OTHER PUBLICATIONS

Manuelidis, PNAS, 1998, vol. 95, p. 2520-2525.*
Nishida et al., J. Virology, 2000, vol. 74, p. 320-325.*
Kanu et al. Current Biology, 2002, vol. 12, p. 523-530.*
Liu et al. The Journal of Biological Chemistry, 2002, vol. 277, p. 47671-47678.*
Enarl et al PNAS, 2001, vol. 98, p. 9295-9299.*
Lehmann et al. Alzheimer's Disease, 2001, p. 679-686.*
Arjona et al., PNAS USA (2004) 101:8768-8773.
Borchelt et al., J. Cell Biol. (1990) 110:743-752.
Bosque and Prusiner, J. Virol. (2000) 74:4377-4386.
Dickinson et al., Nature New Biol. (1972) 237:244-245.
Mange et al., J. Virol. (2000) 74:3135-3140.
Manuelidis and Lu, Neurosci. Lett. (2000) 293:163-166.
Manuelidis and Lu, PNAS USA (2003) 100:5360-5365.
Manuelidis et al., Science (1997) 277:94-98.
Manuelidis, PNAS USA (1998) 95:2520-2525.
Nishida et al., J. Virol. (2000) 74:320-325.
Priola et al., Infect. Agents Dis. (1994) 23:54-58 (Abstract only).
Race, Curr. Top. Microbiol. Immunol. (1991) 172:181-193.
Vey et al., PNAS USA (1996) 93:14945-14949.
Butler et al,, Virology (1988) 62(5):1558-1564.
International Search Report and Written Opinion for PCT/US05/14067, mailed on Feb. 1, 2007, 8 pages.
Priola et al., J. of Virology (1994) 68(8):4873-4878.
Scott et al., Protein Sci. (1992) 1:986-997.

* cited by examiner

*Primary Examiner* — Agnieszka Boesen
(74) *Attorney, Agent, or Firm* — Morrison & Foerster LLP

(57) ABSTRACT

Stable cell lines which produce the pathological form of PrP after infection with the infectious agent for CJD provide a high throughput assay to identify suitable treatment protocols and compositions. The stable cell lines also provide rich source of infectious CJD agent. They also may be used to identify vaccine candidates. Co-culture of neuronal cells with cells to be tested for infection with a TSE agent also provides a high throughput method for identifying infected cells.

8 Claims, 6 Drawing Sheets

HIGH THROUGHPUT ASSAYS FOR TRANSMISSIBLE SPONGIFORM ENCEPHALOPATHIES (TSE)

CROSS-REFERENCE TO RELATED APPLICATIONS

This application claims priority from U.S. Ser. No. 60/564,748 filed 23 Apr. 2004 and from U.S. Ser. No. 60/574,611 filed 25 May 2004. The contents of these documents are incorporated herein by reference.

STATEMENT OF RIGHTS TO INVENTIONS MADE UNDER FEDERALLY SPONSORED RESEARCH

This work was supported in part by grants from the National Institutes of Health and the Department of Defense. The U.S. government has certain rights in this invention.

TECHNICAL FIELD

The present invention relates to compositions and methods for identifying suitable treatment protocols and treatment compositions for transmissible spongiform encephalopathies (TSE). More specifically, the invention relates to stable cell lines which produce the pathological form of PrP (PrP-res) after infection with the infectious agent for a human or other mammalian form of transmissible spongiform encephalopathy, as well as to such stable cell lines which have further been modified to become resistant to an antibiotic. The invention also relates to the use of the stable cell lines in assays to identify compositions and/or protocols for treating transmissible spongiform encephalopathy, and to assess the ability of weaker strains of TSE to behave as vaccines. These cell lines also permit discrimination between various strains of TSE in a more efficient manner than whole animal assays.

BACKGROUND ART

Creutzfeldt-Jakob disease (CJD) is the human form of a group of neurodegenerative diseases collectively known as transmissible spongiform encephalopathies (TSE). These conditions are characterized by high levels of the abnormal form prion protein (PrP) i.e., PrP-res, and have counterparts in bovine spongiform encephalopathy (BSE) and scrapie in sheep. The infectious agents for these conditions have not been identified, but it is known that the infection can be transmitted through the food supply as well as through peripheral routes including white blood cells in experimental animals and humans. Other animals besides humans, sheep and cattle have also been affected by the same or analogous agents, including pigs, rodents, primates, cats and various zoo animals. See, for example, Manuelidis, L., *Science* (1997) 277:94-98. There is no known treatment for these conditions and because humans are at risk with respect to this TSE, the human form is particularly of interest. It would be helpful to provide a high throughput assay to evaluate protocols and compositions that would be useful in treating or preventing this condition in humans and other mammals. The present invention employs successful cell lines as models for the various, including human, forms of this disease.

Cell lines have been prepared from neuroblastoma cell lines that are infected with a scrapie agent which appear to be unstable. Race, R., *Curr. Top. Microbiol. Immunol.* (1991) 172:181-193; Borchelt, D., et al., *J. Cell Bio.* (1990) 743-752. Further, the characteristics of these cells as indicative of infection appear to be unreliable, although these cultures are useful in elucidating metabolism of PrP-res and removal of PrP-res after treatment with selected compounds. See, Priola, S., et al., *Infect. Agents Dis.* (1994) 23:54-58; Vey, M., et al., *Proc. Natl. Acad. Sci. USA* (1996) 93:14945-14949; and Mange, A., et al., *J. Virol.* (2000) 74:3135-3140. Only infectivity related to scrapie has been evaluated in these cell lines, however. The murine hypothalamic GT1 and N2a cell lines have proved more stable with respect to scrapie, but only with specific strains. Bosque, P., et al., *J. Virol.* (2000) 74:4377-4386.

The present invention resides in creating cell lines stably expressing the TSE phenotype, including the appearance of PrP-res. These cell lines are useful in assays to identify compounds that will be effective in treating or preventing the development of TSE, e.g. CJD in humans. Previous reports of reproducibly infected murine hypothalamic GT1-7 cells (hereafter called GT cells) with a number of different scrapie and CJD agents that had been serially passaged in mice are set forth in Nishida, N., et al., *J. Virol.* (2000) 74:320-325; Arjona, A., et al., *Proc. Natl. Acad. Sci. USA* (2004) 101:8768-8773. Stable infection of GT cells did not require cell cloning.

As will be evident below, the invention, in addition to providing cell lines stably infected with a TSE agent for evaluating candidate treatments or for preparing large amounts of the agent itself, also concerns assays to identify potential vaccine candidates as well as methods for identifying a particular strain of agent based on previously observed behavior. These assays reflect the ability of weaker forms of an infectious agent to effect a sort of immunity with regard to more virulent forms, analogous to, for example, vaccination against smallpox, or the use of attenuated virus as a vaccine against polio. Previous work in vivo indicates that similar effects may be seen in TSE infective agents. For example, two strains of CJD have been identified—an attenuated SY strain and a more virulent FU strain. Manuelidis, L., et al., *Proc. Natl. Acad. Sci. USA* (2003) 100:5360-5365. The ability of the SY strain to protect against infection by the FU strain was demonstrated in mice (ibid.).

In TSEs such as human Creutzfeldt-Jakob Disease (CJD), sheep scrapie, and bovine spongiform encephalopathy (BSE), typical cellular and adaptive immune responses to a foreign infectious agent have not been detected (Manuelidis, L., et al., *Science* (1997) 277:94-98). Thus the discovery that SY was able to prevent superinfection by the more virulent and rapidly lethal FU agent in mice was surprising (Manuelidis, L., *Proc. Natl. Acad. Sci. USA* (1998) 95:2520-2525). FU and SY are CJD agents isolated from geographically separate regions of the world. When passaged in mice, these agents were readily distinguished by profound differences in the incubation time to disease, as well as by the distribution of brain lesions. The attenuated "slow" SY agent, propagated from a sporadic CJD case, produced only small medial thalamic lesions, whereas the virulent "fast" FU strain caused widespread severe lesions.

Even with an intracerebral route of inoculation, there was an obvious protective effect of SY against high doses of FU challenge agent. Control mice, first inoculated with uninfected brain and then with FU, all developed widespread FU disease >110 days before any clinical signs were seen in SY protected mice (Manuelidis (1998), supra), and representative brains of SY protected mice failed to show even trace FU agent (Manuelidis, L., et al., *Neurosci. Lett.* (2000) 293:163-166). Moreover, when lower doses of SY doses preceded FU challenge, mice lived without any TSE disease for their entire normal lifespan of >600 days. In contrast, parallel mock inoculated mice all died prematurely of fulminant FU disease 325 days earlier. Similarly clear protective effects of SY were also seen with peripheral routes of infection (Manuelidis (2003), supra).

No comparable interference has been verified using other TSE strains (Manuelidis (1998), supra). Only a small –35 day increase in incubation time was observed with the scrapie strains 22L the 22A inoculated intracerebrally in mice (Dickinson, A., et al., *Nature New Biol.* (1972) 237:244-245). This raised the possibility that the SY CJD agent possessed a unique ability to protect the host.

It would be helpful to have a convenient assay system to determine the possibility that weaker strains of TSE agents can exert a protective effect on infection by more virulent ones. The stably infected cell lines of the invention provide such a high throughput system.

DISCLOSURE OF THE INVENTION

The invention is directed to modified GT1 sublines and N2a cell lines that overexpress murine PrP that have been modified to model the progression of TSE, especially CJD. In one embodiment, the host cell lines are those described in Nishida, N., et al., *J. Virol.* (2000) 74:320-325 and include the murine GT1-1 and GT1-7 sublines (GT1 sublines), and N2a58 neuroblastoma cells.

The invention also includes an important in vitro assay system to detect and identify TSE infective agents harbored in cells that are infective, but that do not produce PrP-res. These cells, such as blood cells and homogenates of various tissues, could previously be assessed in animal studies which require lengthy time periods of up to a year in order to evaluate. The same co-culturing and PrP-res techniques described below in Example 4 are applied to co-cultures of compositions containing cells suspected of harboring TSE infective agents with neuronal derived cells that will, in response to TSE infection, generate PrP-res. Detection of infection can be accomplished within as little as 2.5-3 weeks. In this assay system, the co-culture is assayed for the presence of PrP-res which will result from the transfer of the infective agent from the composition to be tested to the cultured neuronal cells. Advantageously, the co-cultured neuronal cells are modified for antibiotic resistance, especially neomycin resistance. This permits assessment of the co-culture after treating with the antibiotic as the composition containing the cells to be tested will be destroyed, while the neuronal co-cultured cells will not. The determination of generation of PrP-res by the neuronal cells, either as to presence or absence or as to level, thus provides results that indicate the presence, absence, or nature of an infective agent in the co-cultured cellular compositions.

In one aspect the invention is directed to cell lines, such as neuronal cell lines, especially neuroectodermal cell lines, for example GT1-1, GT1-7, and N2a58 cell lines, that are infected with a TSE infectious agent. The cell lines may also be modified to resist an antibiotic, for example, by transfecting these cell lines with a plasmid containing an expression system for an antibiotic resistance gene, such as neomycin resistance.

In another aspect, the invention is directed to a method to identify agents that are effective in prophylactic or therapeutic treatment of TSE which comprises contacting a candidate agent with at least one of the cell lines of the invention and observing the effect of said candidate agent on progress of infection, for example by assessing the levels of abnormal PrP (PrP-res) present. The level of PrP-res is indicative of the progress of the disease and thus, compounds that diminish the level of PrP-res or delay its appearance, as compared to cells treated with control, are identified as agents for treatment of this disease. This assay method can be adapted to a high throughput format, as the times required for disease progression in culture are less than those in vivo and as assessing PrP-res in culture is straightforward.

In another aspect, the invention is directed to co-cultures of first and second cell lines infected stably with different strains of TSE agent. In one embodiment, one of the cell lines is further modified to become resistant to an antibiotic that would otherwise be cytotoxic to the host cell. The co-cultures are useful in evaluating candidate protective agents against particular TSE agents. Thus, in one embodiment, one of the two cell lines (a target cell line) will contain a candidate protective TSE agent, and the other a challenge TSE agent. The ability of the infection by the candidate to protect the host cells against infection by the challenge can be assessed by, for example, measuring the level of PrP-res in the cell line comprising the candidate. The efficiency of this system can be improved by modifying the candidate comprising target cell line to be antibiotic resistant so that subsequent to challenge, the challenge cell line can be destroyed, and the effect of the challenge on the target more easily analyzed. The co-cultures are also useful in distinguishing types of TSE agents based on previous results of interaction between individual strains. The invention is also directed to methods to identify protective agents using infected tissue to challenge the stably transfected cells harboring candidate less virulent TSE agents.

The stably infected cell lines of the invention also provide a rich source of infectious TSE agents, such as CJD agent. Accordingly, another aspect of the invention is directed to a method for producing a high number of infectious CJD and related TSE agents and a method for producing and/or isolating a highly concentrated sample of infectious CJD and related TSE agents. The invention is also directed to compositions comprising high numbers of infectious CJD and related TSE agents.

In still another aspect, the invention is directed to a method to demonstrate the presence of infectious agents in cells that do not produce PrP-res. Whole cells, such as white blood cells, can be demonstrated to be infective by co-culture with target cells that produce PrP-res. Previously, the infectivity of these cells, such as blood cells, would be demonstrated on animal experiments where more than 300 days are required to obtain results. However, using the co-culture method of the invention, the ability to infect co-cultured cells, including co-cultured cells that have been made antibiotic-resistant to simplify the assay, can be obtained after approximately only three weeks.

The co-culture methods of the invention have been demonstrated to show infectivity at dilution levels comparable to those that can be seen in mice; whereas the murine assay takes more than 250 days to see the results of a $10^6$ dilution of infected brain, the cell culture assay provides results after 21-28 days at this dilution.

MODES OF CARRYING OUT THE INVENTION

Figure 1:
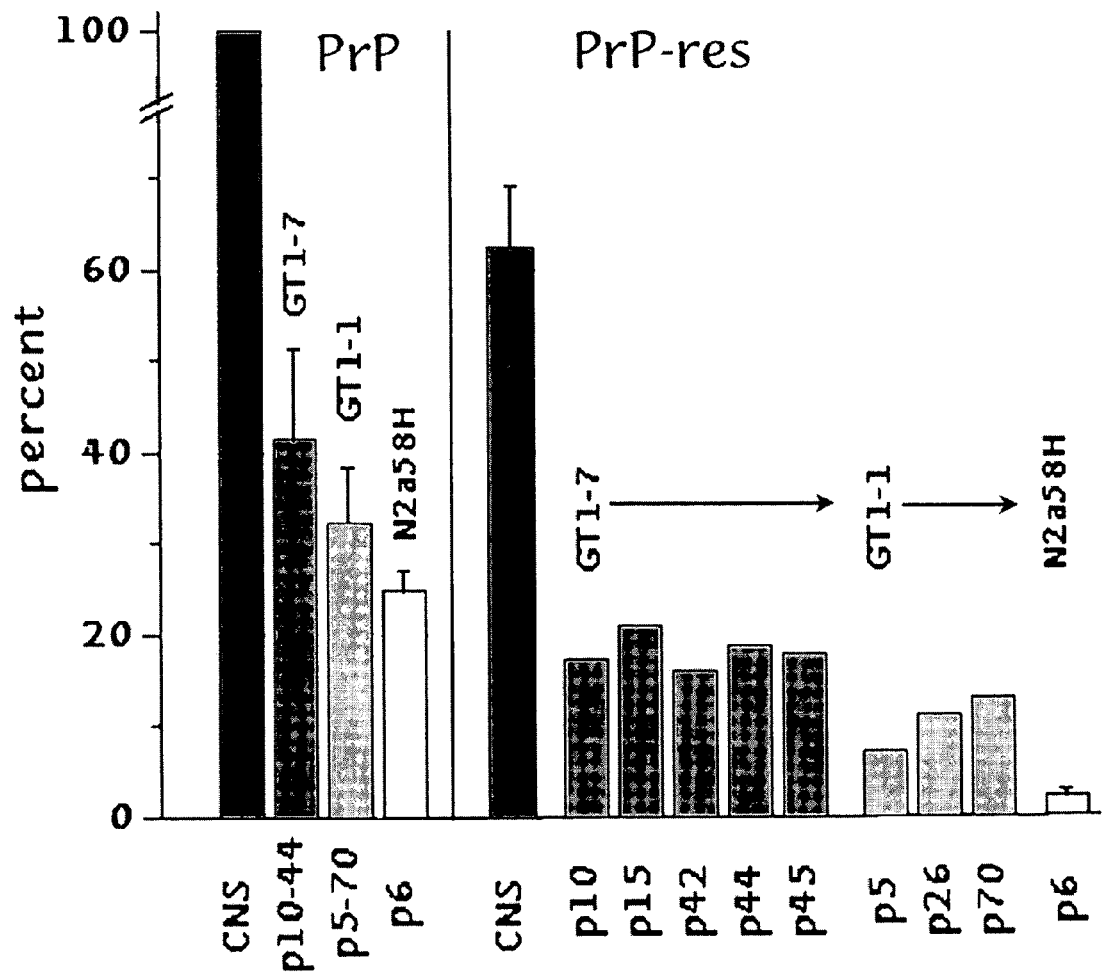
FIG. 1 shows quantitation of total PrP and the abnormal form thereof (PrP-res) as the cells of the invention are passaged.

The invention provides, for the first time, stably infected cell lines that can serve as surrogates for animals infected with human or other mammalian forms of TSE. By culturing these cell lines and assessing the effect of candidate protocols and agents on the progress of infection, typically by measuring the timing and/or amount of their production of abnormal PrP as compared to controls, successful candidate protocols and compositions are identified.

The cell lines are obtained by infecting the host cells with infected brain homogenates and growing them as described in the examples below. Levels of PrP-res can be detected in situ in the most efficient and rapid form of such assays. Alternatively, the cells may be lysed and the quantity of abnormal PrP in the lysate detected by methods that distinguish between normal and abnormal PrP. Details of an illustrative method to perform such analyses are set forth in the examples below.

Antibodies specific to the various forms of PrP are known in the art. Abnormal PrP may be recognized by antibodies disclosed by Manuelidis, L., et al., *Science* (1997) 277:94-98; antibodies which recognize normal PrP amyloid are available for purchase. Alternatively, antibodies, either polyclonal or monoclonal, can be prepared using standard art-known techniques by immunizing suitable subjects and titrating plasma to obtain polyclonal preparations or by immortalizing antibody-producing cells and screening for monoclonal antibodies.

Details of these various techniques are found in the examples below. It will be evident that in view of the variability of the appearance of PrP-res as a function of time, control cells not contacted with the compositions to be tested should be employed simultaneously with the screening assay. The assay, however, offers a high throughput method to assess the efficacy of treatment protocols.

The host cells that are infected to obtain the cell lines containing stable infection are preferably derived from the neuronal system, for example neuroectodermal cells. Illustrated below are two specific cellular types, GT cells and N2a cells; however, the hosts are not limited to these. Other neuronal cell lines are also suitable hosts. The stably infected cell lines typically exhibit the phenotype of TSE-infected cells. Among the features of this phenotype is the presence of abnormal PrP (or PrP-res). PrP can readily be distinguished from PrP-res by their differential reactivity with regard to the antibodies described above, as well as the resistance of abnormal PrP to proteolysis.

A large number of strains of TSE agents are known, which are used herein to create stable cell lines. Those used in the illustrative samples below include two human strains—a fast-acting strain designated FU, and a slow-acting strain designated SY. Also included in the illustrative examples are scrapie agents Ch and 22L. Other agents, such as those associated with BSE and the disease in other mammals can be used as well. Human TSE strains are of particular interest in view of the catastrophic health problems caused by the human form of this condition.

One aspect of the invention relates to the ability of weaker strains of a TSE agent to protect against infection by a more virulent strain. By a "more virulent" strain is meant one that effects higher production of PrP-res and/or more immediate production of PrP-res and/or results in earlier death or earlier exhibition of other symptoms. For convenience in the high throughput assays of the invention, the length of time required for the appearance of PrP-res and/or the levels of PrP-res produced are convenient measurements of the progression and virulence of the disease. "More virulent" also has an element of host specificity. For example, forms of the agent that are active in sheep, such as scrapie strains, may be less virulent in humans. Thus, the ability of a scrapie strain to protect against infection by a human strain is, in effect, protection by a less virulent strain.

Candidate compositions and protocols for treatment of a TSE-caused disease may exert either therapeutic or preventative effects or both. Compositions which might be tested are small molecules, i.e., the type of molecule generally found among approved drugs in the U.S. pharmacopoeia, as well as peptides, proteins, various nucleic acid-based compositions, or any substance or mixture of substances that might inhibit the progress of the disease. As described below, in one aspect, the candidate composition may be a less virulent form of TSE than that for which protection or amelioration is desired. The less virulent form may be inherently less virulent, or it may derive from the same causative agent in an attenuated form.

Cultures of stably transformed cells, then, can be characterized as cultures containing target cells where the effect on these target cells of various perturbations can be assessed. The target cells of the invention are stably infected with a TSE agent; the candidate composition or protocol may be a simple composition or alteration in media conditions, temperature, pH, or formulation, that is designed to ameliorate the infection. The target cells may also be modified to contain genes which confer antibiotic resistance. These cells are particularly useful when assessed in co-culture with cells carrying substances or infective agents that are designed to challenge the target cell. If these challenge cells are not modified for antibiotic resistance, the antibiotic may be used to treat the co-culture whereby the challenge cells are killed, but the target cells are not. This eliminates a complicating factor in assessing the progress of infection in the target cells, as the challenge cells are no longer present to complicate the results.

Some of the cell lines stably infected with a TSE agent have been described in Arjona, A., et al., *Proc. Natl. Acad. Sci. USA* (2004) 101:8768-8773. Preferred hosts are neuroectodermal cells.

In a typical experiment, a co-culture of target cells already provided with a mechanism for resisting infection, for example a weakened form of the infective agent, are co-cultured either with challenge cells which contain a more virulent form of the agent or with tissue that is already infected with this more virulent form. In one embodiment, the target cells are antibiotic resistant, and the challenge is provided by co-cultured infected cells. After co-culture of the target and challenge cell lines, the challenge cell line is eliminated by treating the culture with an antibiotic and suitable measurements can then be conducted on the culture with results characteristic of the target cell alone.

As shown below, target cells that contain a weakened form of the human TSE agent SY exhibit resistance to challenge by a more virulent agent. The evaluation of this protection takes only about three weeks, as compared to more than 300 days (almost a year) for similar assays conducted in vivo.

In addition to initial identification of strains of TSE agents that are protective with respect to more virulent ones, results of these assays can be used in future determinations to distinguish strains of TSE agents. As shown in the Examples below, the 22L scrapie strain was able to protect against infection with the more virulent FU strain, whereas the Ch scrapie strain was not able to do so. Thus, the co-culture assay of the invention can be used to distinguish quickly between these two strains by assessing their ability to protect against FU.

The residual pure GTneo target cells could then be assayed by Western blotting for PrP-res, a surrogate marker for positive infection in GT cells. Although PrP-res does not quantitatively correlate with infectious titers, and may not be detectable in all infectious samples, its presence does indicate infection in GT cells.

This high throughput method for assessment of infection in neuronal cells in culture can also be used to assess the infectivity of cells that do not themselves produce PrP-res. Thus, a culture of such cells is co-cultured with cells suspected of containing infection. These cells may be blood cells, such as white blood cells, or other types of cells or tissue homogenates that normally do not produce PrP-res. By the co-culturing method, the neuronal cells, preferably protected by modification to be antibiotic-resistant, can be assessed for acquiring the infection from the suspected co-cultured cells after a very short period of about three weeks, as compared to the almost year-long time frame required for animal experiments. As noted above, the sensitivity of this assay is comparable to that attainable in whole animal assays to levels of approximately $10^6$ dilutions of infected brain tissue.

As demonstrated in the Examples below, PrP-res is not itself infectious, although abnormal PrP-res is often claimed to be. The Examples show that cells containing particular TSE agents themselves are infectious and that certain TSE agents are protective. The protective effect observed could involve the production of defective interfering particles produced by particular TSE agent strains. Defective viruses have been found in many viral infections, and they have been associated with both viral persistence and the modulation of the disease. The attenuated SY agent, that yields very low infectious titers, may generate thousands of replication incompetent or empty particles for each complete infectious particle. These defective particles could produce a bottleneck at membrane sites needed for the transit and maturation of the challenge agent. These empty particles would not co-purify with virus-like infectious particles, and any strain-specific protein on these particles would be very difficult to detect among the plethora of complex cell membrane proteins. Alternatively, the defective particle might be a mutant or truncated viral RNA, analogous to the RNAs made by retroviruses that have manifold mechanisms of interference. Even simpler defective RNAs have been recently described for the small hepatitis delta satellite virus.

However, applicants do not intend to be bound by any particular theory to explain the protective effect.

As noted above, the same techniques described in Example 4 in evaluating interference with TSE infection by co-culturing target cells with challenge cells can be used in an assay to detect the presence, absence, nature, or level of TSE infective agent in a cell containing sample. The cell containing sample is co-cultured with neuronal cells, thus permitting the transfer of the infective agent from the test cells to the recipient neuronal cells. As the neuronal cells are able to generate PrP-res, determination of the appearance, non-appearance, or level of PrP-res can be used as an index to ascertain the infection status of the donor cells to be tested. This assay system is much more efficient than the animal-based systems and permits determination of responses within three weeks.

The following examples are offered to illustrate but not to limit the invention.

Example 1

Preparation of Infected Cell Lines

Murine GT1-1 and GT1-7 sublines from immortalized hypothalamic GT1 cells were trypsinized and split 1:4 or 1:5 weekly. N2a58 neuroblastoma cells overexpressing wt murine PrP were trypsinized and split 1:10 every 5 days. These cells are described in Nishida, N., et al., *J. Virol.* (2000) 74:320-325 (supra). Cell lines were fed high glucose DMEM with 10% heat inactivated fetal bovine serum with 1% penicillin-streptomycin (Gibco™, Life Technologies). Cells at 50% confluence in 6-well plates were exposed for 24 hr to 1% or 2% normal or infected brain homogenates in medium, washed, grown to 90% confluence, and then transferred to a 25 $cm^2$ flask (p1). Infected GT1 sublines were not subcloned. N2a58 cells were diluted at p1 and seeded at 0.7 cells per well in 96-well plates. Single cell clones were screened for PrP-res (detected in 21% of the clones, n=48), and a clone with the strongest signal (FU N2a58H1) was selected for further expansion in parallel with a clone from mock N2a cells (N2a58#1). The amount of total PrP, and of PrP-res, relative to that found in FU infected mouse brain was determined using whole cell lysates to avoid inaccuracies from subcellular fractionation. The left panel of FIG. 1 shows the amount of total PrP in brain as a 100% standard per mg cellular protein. The expression of PrP was less in the sublines than in brain, and, as can be seen from the SEM's, varied less than 2 fold when sampled every 10-15 passages. Mock controls showed the same amounts of total PrP (data not shown). The PrP-res in each FU infected cell line was also less than in brain (right panel), and varied little after its first appearance. Notably, PrP-res in different passages of GT1-7 and GT1-1 all showed <2 fold changes in PrP-res with progressive subculture.

Example 2

PrP and PrP-res Patterns in Cell Lines

Whole cell lysates prepared from the cells of Example 1 were treated for 30 min with proteinase K (PK) at 25-30 μg/ml to obtain maximal amounts of PrP-res for Western blotting. Protein was determined by Bio-Rad DC protein assay, and quantitation of PrP bands was done on films in the linear range. For deglycosylation, SDS denatured proteins were digested with 10 units of PNGase F (Sigma) overnight at 37° C. If necessary, proteins of >12 kd were quantitatively precipitated with 6 vol of EtOH and centrifugation at 19,000 g×45 min at 4° C. PrP on blots was evaluated with four PrP antibodies: i) a rabbit antibody raised against the amino terminus (aa23-30) of PrP (IBL Ltd., Japan), ii) a rabbit polyclonal antibody recognizing PrP-res amyloid (Manuelidis, L., *Science* (1997) 277:94-98), and iii & iv) two goat polyclonal antibodies recognizing the carboxy end of PrP amyloid (aa 91-200; C-20 and M-20, Santa Cruz). Biotinylated lectins (Vector Labs) were used to verify removal of sugar residues (Sklaviadis, T., et al., *Proc. Natl. Acad. Sci. USA* (1986) 83:6146-6150).

Representative data for PrP-res at different passages are shown in FIG. 2A. N2a58H cells, with the lowest expression of PrP had the lowest amount of PrP-res, and brain PrP-res was 62%, of total PrP, in good accord with previous determinations. Mock controls, treated with normal brain in parallel, showed no PrP-res (FIG. 2B, lanes 11 & 12, and 2C, lanes 4-6).

Figure 2:
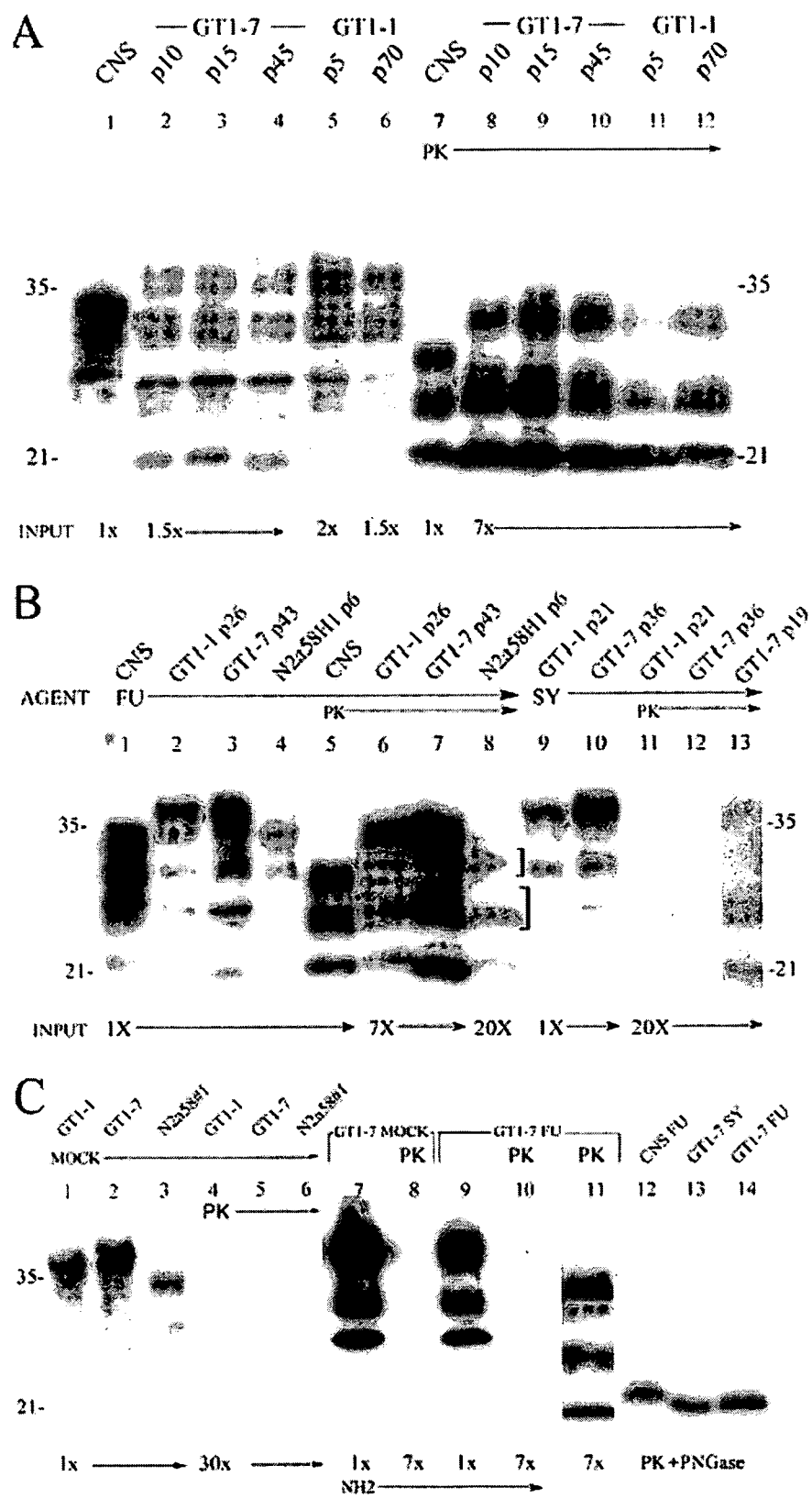
FIG. 2 shows Western blots of whole cell lysates from brain and cell lines at different passages, showing the pattern obtained as a function of the passage number and strain.

Total cellular PrP, as well as PrP-res, had markedly different banding profiles by Western blotting in cell lines as compared to brain. In FU and SY infected mouse brain, PrP-res shows identical band mobilities and glycoform ratios and hence does not discriminate these two very different agents. FIG. 2 shows PrP from brain (FIG. 2A, lane 1 & 2B, lane 1) and representative passages of GT1 and N2a sublines (FIG. 2A lanes 2-6 & 2B, lanes 2-4). There are striking differences in intensity and Mr of bands. There are also obvious differences between the Mr of PrP-res bands as well as their glycoform ratios in brain and cell lines (FIG. 2A, lanes 7-12, 2B, lanes 5-8 & legend). Both FU infected GT1 sublines show the same PrP-res pattern, but FU infected GT1-7 has about twice the amount of PrP-res as compared to GT1-1 cells (FIG. 2A, lanes 8-12). GT1-7 cells challenged with slow SY showed only a weak PrP-res signal and this appeared only at later passages 13 to 19 (FIG. 2B, lane 13). This PrP-res signal was lost after p19 (lane 12). Moreover, the Mr of PrP-res bands from FU and SY in GT1-7 cells were the same in three independent analyses, again indicating the PrP-res pattern is cell type rather than agent specific.

To assess if the more resistant amyloid core was retained and all the susceptible amino-terminal PrP was completely digested, blots were probed with antibodies to both the amyloid and amino terminal regions of PrP. The two amyloid core antibodies showed the same bands whereas after PK, even at 7× gel loads, no amino terminal PrP was detectable (FIG. 2C, lanes 7-11). The cell type specific PrP-res band patterns did not change with passage (FIG. 2A). We also tested if the different sizes of PrP-res bands in cells were due to differential glycosylation. This post-translational modification has been proposed to encode strain-specific properties, despite the fact that PrP deglycosylation alters neither the infectious titer nor the strain characteristics of a CJD agent. FIG. 2C, lanes 12-14, shows the complete deglycosylation of representative PrP-res samples. The higher Mr bands in GT1 cells as compared to brain were due to increased glycosylation. There was only a single low Mr band after deglycosylation with PNGase. Lectin staining also verified the deglycosylation of PrP-res, but not of many other PK resistant proteins. Despite agent strain differences, deglycosylated PrP-res was the same in FU and SY infected GT1-7 cells, as in brain. However, GT1 cells showed a 1-2 kd lower Mr than infected brain, presumably caused by sugar residues on PrP during PK digestions. Hence it might be predicted, according to the prion hypothesis, that the agent strain passaged in GT1 cells should give rise to a variant agent strain when inoculated into mice.

Example 3

In Situ Detection of Pathologic PrP

Because cells detached and became morphologically disrupted using GdnHCl and PK treatments, methods for PrP-res detection in paraffin sections were modified. Cells in flasks were fixed in situ with 4% fresh paraformaldehyde in PBS for 10 min, scraped, pelleted at 4,000 g×10 min, and then fixed for an additional 12-16 hrs before paraffin embedding. Slides were autoclaved in citrate buffer, digested with 0.002-0.004% trypsin 7-15 minutes, quenched, exposed to antibodies, and developed with Vector Red. FU and mock infected control cells were mounted on the same slide.

Figure 3:
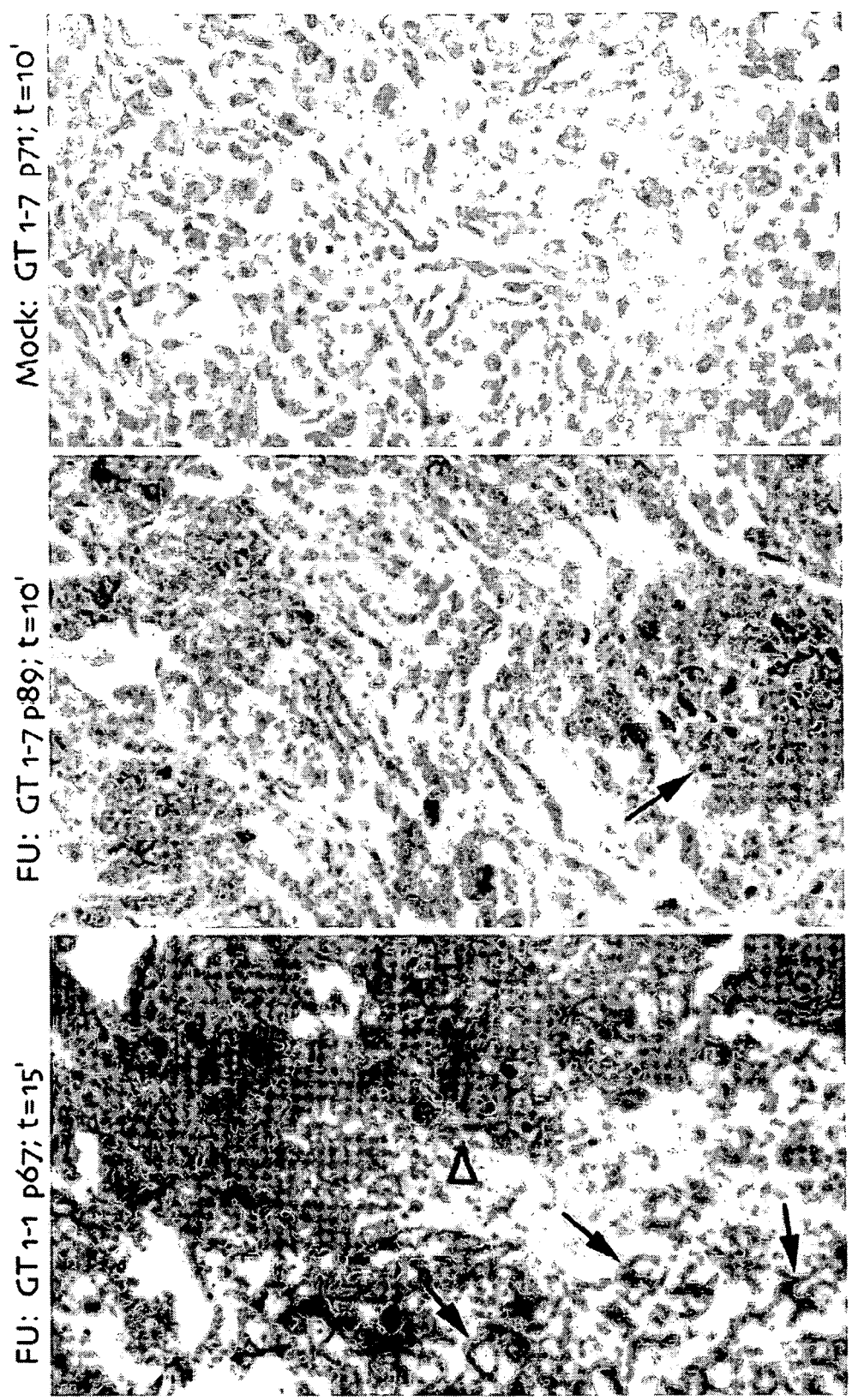
FIG. 3 shows in situ detection of PrP-res in mock and infected cell lines.

To visualize PrP-res in individual cells, and thereby estimate the percentage of infected cells, we evaluated cell pellet sections treated with trypsin. Limited trypsin digestion left only the amyloid core of pathologic PrP intact. FIG. 3 shows representative mock and FU infected cells probed with an antibody to the carboxy portion of PrP-res. The amino terminal antibody, as in Western blots of FIG. 2C, showed no signal, indicating complete removal of non-amyloid portions of PrP (data not shown). Mock cells displayed no abnormal PrP-res aggregates (top panel). In contrast, FU infected GT1-7 and GT1-1 cells displayed abundant PrP-res aggregates in >30% of cells. In GT1-7 cells, PrP-res formed compact aggregates within the cytoplasm (arrow, middle panel). About 30% of the cells showed these PrP-res aggregates. This is probably an underestimate of infected cells since sections will not sample all such aggregates. FU infected GT1-1 cells exhibited a strong, but more diffuse staining throughout the cytoplasm (arrows, bottom panel), although a few cells showed the more compact PrP-res aggregates (open triangle). A high proportion of FU GT1-1 cells were PrP-res positive ($\geq$50%), and since cells were fixed in situ before scraping, the closely associated positive cells may reflect cell to cell spread of agent. There were a few more pyknotic nuclei in infected GT1 sublines as compared to mock controls, possibly due to high levels of infection and/or secondary to pathologic PrP-res accumulation, but the vast majority of cells were morphologically normal. Thus these cells can be advantageous for agent-specific studies, as they are not visibly compromised by the degeneration found in end-stage brain. Although not quantitative, these in-situ results are consistent with previously determined ratios of ~100,000 PrP-res molecules to each infectious dose.

Example 4

Co-Cultures and Protective Effect of Weakened Strains

This example describes the ability of weaker strains of TSE agents to interfere with infection by more virulent strains at the cellular level, using the stable cell lines of the invention.

Table 1 shows the cell lines used to test interference. The infectious encephalopathy agents and their source are shown, as well as the number of cell passages post infection at the time interference was tested. Ch is the UK Chandler scrapie agent (often referred to as RML in the USA). FU (also known as FK-1) was isolated from a patient in Japan with Gerstmann-Straussler-Sheinker Disease (GSS) and a 102L mutation in his PrP gene. This FU agent produces widespread brain lesions 120 days after mouse inoculation ic, while SY produces circumscribed thalamic lesions only after 350 days. The Ch and 22L scrapie strains, as FU, also produce rapid disease in mice with widespread brain pathology, making interference between these strains impossible to assess in vivo. Infectious titers of SY and FU after extended in vitro splits were previously determined and FU showed >1,000 fold more infectivity than SY in vitro. Arjona, A., et al., *Proc. Natl. Acad. Sci. USA* (2004) 101:8768-8773 (supra). Bioassay titers for 22L in cells cultured for >100 passages was higher than in brain or FU infected cells (results reproduced independently in US and Japan, data not shown).

TABLE 1

Cell lines and TSE agents

| | Cell line | Infectious TSE agent strain | Infectious TSE agent origin | passages post in-fection |
|---|---|---|---|---|
| Chal-lenge: | GT (GT1-7) | — | | |
| | SY + GT | SY | sporadic CJD in USA | ≧106 |
| | FU + GT | FU | GSS 102L in Japan | ≧110 |
| | Ch + GT | Ch (RML) | drowsy scrapie in UK | ≧50 |
| | 22L + GT | 22L | scrapie in UK (SSBP/1) | ≧50 |
| Targets: | GTneo | mock | | |
| | SY + GTneo | SY | sporadic CJD in USA | >110 |
| | Ch + GTneo | Ch (RML) | drowsy scrapie in UK | >15 |
| | 22L + GTneo | 22L | scrapie in UK (SSBP/1) | >15 |

The results obtained in the experiments described below can be summarized in Table 2. In this table, + indicates strong PrP-res signal (positive infection), − indicates no detectable PrP-res, and (+/−) indicates ⅓ experiments where there was a very weak PrP-res signal. C-13 is a 13 kd band that is diagnostic for FU superinfection.

TABLE 2

Summary of Interference Experiments

| agent target | agent challenge | PrP-res PrP-res (total) | PrP-res C-13 | Interference |
|---|---|---|---|---|
| Mock | FU | + | + | No |
| Mock | 22L | + | − | No |
| Mock | Ch | + | − | No |
| SY | Mock | − | − | No |
| SY | FU | −(+/−) | − | Yes |
| SY | 22L | −(+/−) | − | Yes |
| SY | Ch | −(+/−) | − | Yes |
| 22L | FU | + | − | Yes |
| Ch | FU | + | + | No |

As expected, unaltered GT cells were readily infected by FU, 22L, and CH. Target cells that had been modified by the weak TSE agent SY appear protected against infection by all three tested strains. Small amounts of PrP-res were sometimes seen as described below, but in general, PrP-res was absent. The diagnostic C-13 band in protected targets was not present when co-culture with an FU bearing strain was performed. Thus, SY was able to interfere in all cases where challenge was supplied. Of course, there was nothing to protect against when mock challenge was done.

Finally, the table shows that 22L was able to protect against FU infection, but Ch was not.

Figure 4:
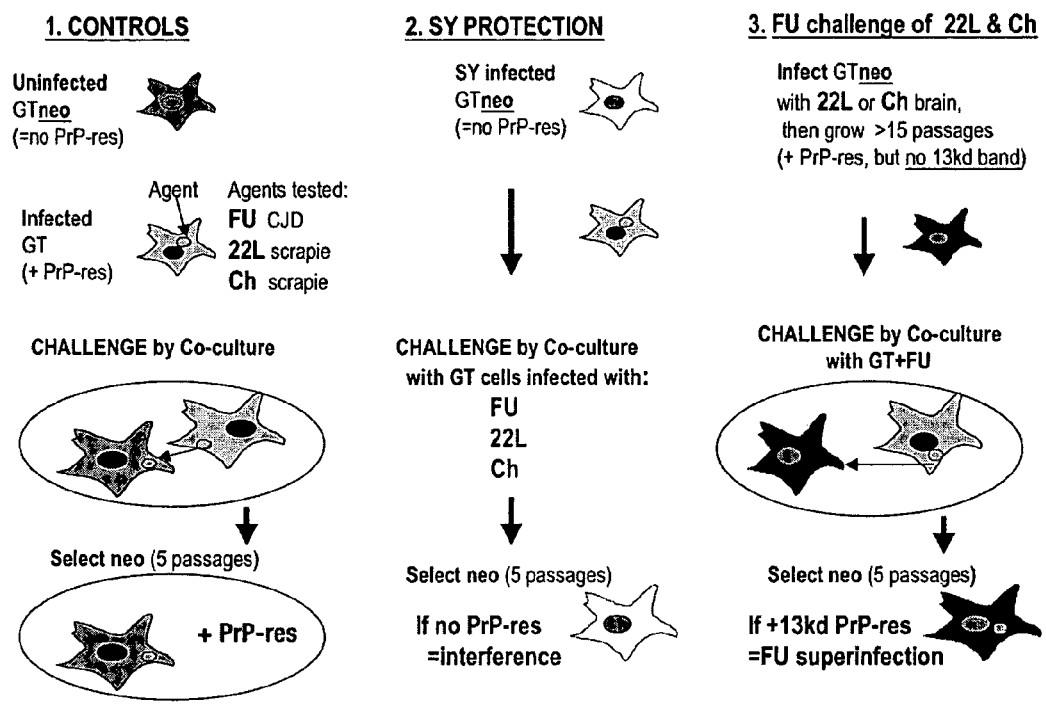
FIG. 4 is a diagrammatic representation of the co-culture method of the invention.

FIG. 4 outlines in more detail the in vitro interference strategy used in this example. Target GTneo cells were co-cultured with uninfected (mock) GT, or infected GT challenge cells for two days, and the GT challenge cells were then killed by G418 antibiotic treatment. (In control experiments GT cells were completely eradicated by G418 in 10 days.) At 21 days (5 passages), the screening target GTneo cells were collected for PrP and PrP-res Western Blot analyses. Assays were also done at more extended passages to test if PrP-res increased. The infected challenge GT cells used were persistently infected for 1-2 years and continued to have high levels of infectivity when assayed by mouse titration. A neomycin resistant plasmid was introduced into persistently infected SY GT cells for experiments in column 2, and GTneo cells were newly infected with scrapie 22L and Ch brain homogenates then passaged >15 times before testing interference against FU as outlined in column 3.

Neomycin (neo) resistant GT cells, both uninfected and SY-infected, were established by introducing the plasmid pEGFP-C1 (Clonetech) with Effectene transfection reagent (QIAGEN) according to manufacturer's instructions. The GT+SY cells had been continuously subcultured more than 106 passages and shown to be persistently infected. Resistant clonal cells were isolated by selection with 500 μg/ml of G418 (GIBCO BRL). Neo-resistant GT cells were incubated with 0.2% mouse brain homogenates to produce mock and infected GTneo cells as previously described (Nishida, N., et al., *J. Virol*. (2000) 74:320-325) from end stage brain infected with the 22L scrapie agent or the Chandler (RML) scrapie agent. These cells were used for experiments after stable infection was confirmed by Western blotting for PrP-res at passages 10 and 15 in vitro. All the different GT cell lines (GT and GTneo, uninfected and infected) were morphologically the same and showed the same doubling time. They were passaged as previously described (supra).

GTneo target cells were co-cultured with GT challenge cells that were mock-infected, or infected with the TSE agents shown in Table 1. GT+FU cells have been maintained for more than 2 years and showed persistent high titers of infectivity. On the day before starting co-culture experiments, $1\times10^6$ neo-resistant target cells were plated in a T25 flask, and then overlayered with same number of the challenge cells on the next day. The co-cultures were incubated for 2 days at 37° C., 5% $CO_2$, in medium without antibiotic. To eradicate challenge GT cells from the culture, the cultures were repeatedly split at a 1:3 dilution while being treated with 500 μg/ml G418 at each passage. Some neo-sensitive cells started dying on the first day, but the killing effect of G418 was gradual, and 60% of GT the cells were eliminated by 5 days of treatment. Therefore significant numbers of challenge cells were present in co-cultures for 7 (2+5) days. We confirmed that neo-sensitive cells were completely eradicated by day 10th day of treatment with G418 (by parallel culture). Thus assay for more than 5 passages (3 weeks) in G418 antibiotic ensured all PrP-res originated only from GTneo target cells.

After 5 passages the confluent GTneo cells in a T25 flask were washed twice with cold PBS- and lysed with 500 μl of Cell-lysis buffer: 0.5% Triton X-100, 0.5% sodium deoxycholic acid, 150 mM NaCl, 50 mM TrisHCl pH 7.5, 2 mM EDTA. Cell lysates were spun at 3,000 RPM for 5 min to remove nuclei and insoluble material. This also removed some large PrP aggregates as determined by Western blotting (data not shown). After normalizing the supernatant protein concentration to 1 mg/ml, 500 μl of each sample was treated with 10 μg of proteinase K (20 μg/mg protein) (Bohringer) for 30 min at 37° C., and the digestion stopped by adding 3 mM PMSF. All the PK-digested samples were then centrifuged at 20,000×g for 45 min at 4° C., and the pellets were resuspended in 30 μl of 1× Laemmli sample buffer. SDS-PAGE and Western blotting were done with 50 μg of protein loaded per sample. For detection of PrP in undigested total cell lysates the membrane was incubated with the SAF32 monoclonal antibody that recognizes the octapeptide repeat region (supplied by Jaques Grassi, France), and the polyclonal M-20 antibody (Santa Cruz Biotech, CA) that recognizes a C-terminal region of PrP was used to detect PrP-res. The extra 13 kd C terminal band of PrP-res in FU had not been appreciable in digested whole cell lysates previously and the double centrifugation (fractionation steps here, as well as the use of Triton-X 100 rather than NP-40), led to the relative enrichment of this PrP-res band. It did not bring out the 13 kd band with any of the other strains.

Infectivity assays of cells infected with SY and FU were done as described and reported (Arjona (2004), supra), and the same bioassay methods were used to test 22L infected cells. These cells also had similarly high or higher levels of infectivity per cell than brain and GT+FU cells (independent assays in Japan and USA, data not shown).

Figure 5:
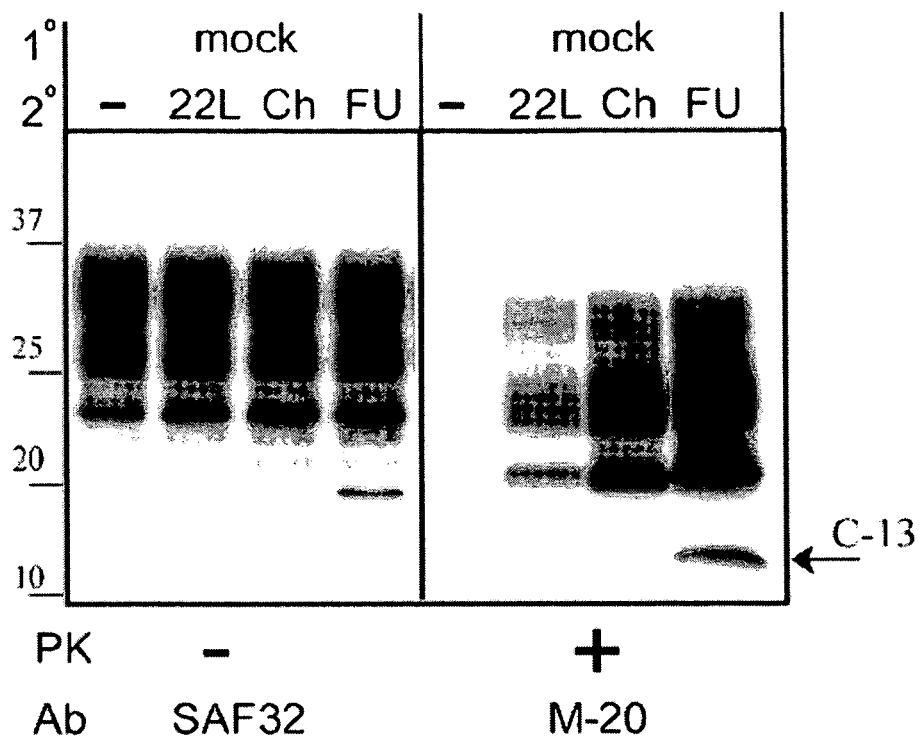
FIG. 5A shows the levels of PrP and PrP-res in target cells co-cultured with challenge TSE infected cells, where the target cells are wildtype.
FIG. 5B shows similar results where the target cells have been infected with SY.
Figure 5:
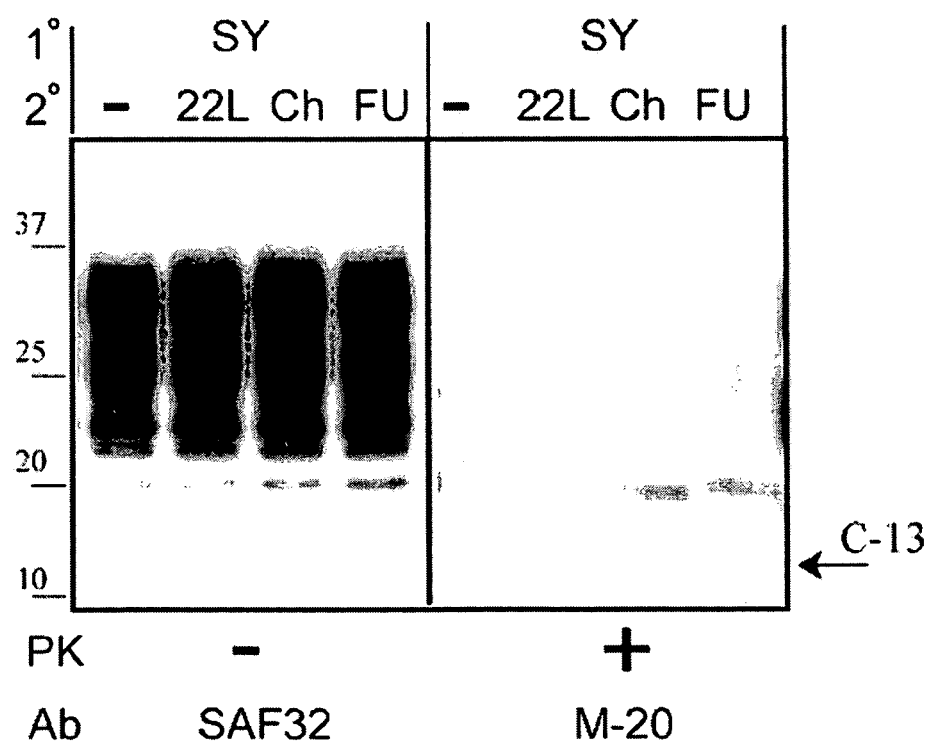

FIG. 5 shows the results of co-culture of mock (5A) and SY infected (5B) GTneo cells, as well as with equal numbers of uninfected GT cells (−) or infected GT+22L, GT+Ch and GT+FU cells as indicated. After 2 days co-cultures were treated with G148 to select for GTneo target cells and passaged 5 times before assays for undigested PrP (left panels) and digested PrP-res (right panels). 1° indicates the primary infection and 2°, the challenge infection. PrP-res indicates positive infection. The C-13 band appeared only in FU infected cells. PK indicates limited proteinase K digestion, and SAF-32 and M-20 antibodies (Ab) were used for PrP and PrP-res detection, respectively. There is minimal or no PrP-res in SY protected cells as compared to controls. Markers in kd are indicated at left.

Thus, FIG. 5A shows a representative example of the large amount of PrP-res produced by GTneo mock cells after they had been challenged with infected GT cells and then treated with G418. The left half of the figure shows undigested PrP in GTneo cells challenged with uninfected brain (−), or with GT+22L, GT+Ch, or GT+FU infected cells. All cells express similar amounts of PrP. The right side of the blot shows PrP-res in these detergent lysates after limited proteinase K (PQ digestion and centrifugation of aggregates at 20,000 g. There is a large amount of PrP-res produced by cells exposed to each of the infected GT cell lines, whereas no PrP-res is seen in the cells (−) challenged only by uninfected cells. Further in vitro passages of these selected GTneo cells did not alter these findings, indicating that the mock cells were persistently infected by each of the challenge agents. The three major PrP-res bands are the same in all infected cells. However, FU infected samples showed an extra minor 13 kd band (labeled C-13), and this allowed diagnosis of FU superinfection in subsequent challenge infection.

In summary, control experiments showed rapid infection with de novo production of large amounts of PrP-res by 21 days after co-culture challenge. (In mice infected with the virulent FU agent intracerebrally, it takes >90 days to detect any PrP-res in brain.) More than 95% of homogenate infectivity is cleared from brain within 24 hours and living cell-to-cell contacts may enhance the transfer TSE agents.

FIG. 5B shows a representative blot of PrP and PrP-res after challenge to SY protected GTneo cells, with protein loads and conditions the same as in 5A. SY infected cells had no detectable PrP-res, and this greatly simplified the interference assay, since after challenge by co-culture, a continued lack of PrP-res would indicate this covert SY infection interfered with transmissions from GT cells loaded with much higher levels of challenge agent. It is obvious that there is no detectable PrPres in SY infected cells after co-culture with 22L scrapie infected cells. The lack of PrP-res also shows that the G418 selection regime was able to completely remove PrP-res positive challenge cells. The failure to display PrP-res after challenge is strong evidence that the SY agent prevented superinfection by this particular 22L scrapie agent. With GT+Ch scrapie agent and GT+FU agent challenges, there was a very small amount PrP-res as compared to mock controls. Such a low level of PrP-res showed SY infection had substantially interfered with superinfection by the Ch scrapie and FU agents, but that the protection might not be absolute. This apparent "leakiness" could be due to the relatively low infectivity of SY. Alternatively, the low levels of PrP-res detected after Ch and FU challenge could reflect increased activation of the SY agent resulting from the stress of challenge itself. Such increased SY activation, with consequent host production of pathologic PrP-res cannot be excluded, because we have found certain chemical stresses alone can educe similar low levels of PrP-res in persistently infected SY cells (unpublished data).

Further passages did not increase the low amount of PrP-res in either the PrP-res negative cells (−) or in the cells with very low PrP-res (+/−) as summarized in Table 2 alone. Additionally, the 13 kd PrP-res band elicited by FU infection was not detectable in the FU challenged SY cells, and the lack of any distinguishing strain-specific PrP-res patterns for the other three common major PrP-res bands made it impossible to determine if the low amounts of new PrP-res in were due to low levels of superinfection, or to increased SY activation. In two additional repeat experiments, SY again interfered either completely, or almost completely, with superinfection by 22L, Ch and FU agents. However, perfect interference was inconsistent with respect to each agent strain. In the repeat experiments, complete prevention of Ch and FU superinfection was found at least once, and extensive but incomplete interference was observed once with 22L scrapie agent challenge. The results summarized in Table 2 are consistent with animal experiments showing dose dependence and/or slight leakiness of the SY infection in the target cells.

Figure 6:
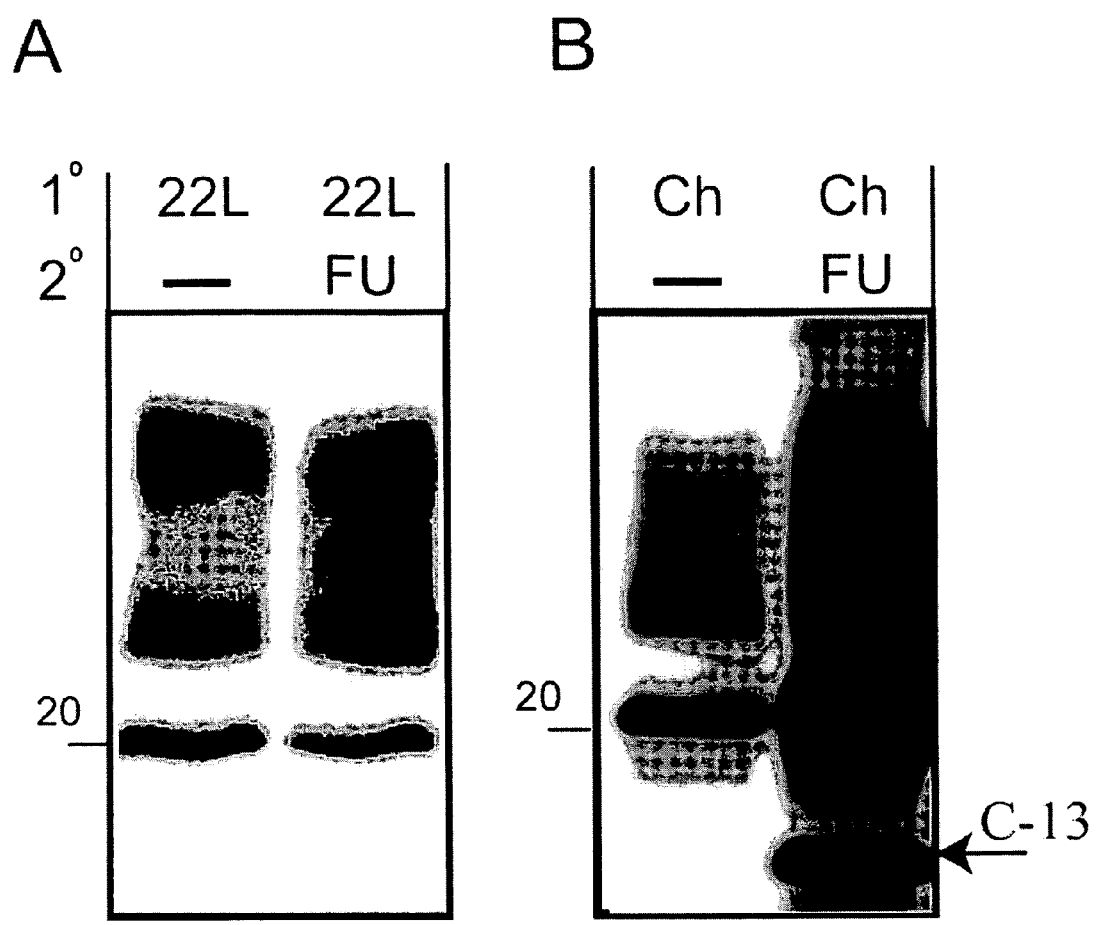
FIG. 6A shows results of PrP-res determinations indicating that infection of target cells with 22L is protective against FU infection.
FIG. 6B demonstrates that infection of target cells with the scrapie strain Ch is not protective.

FIG. 6 shows the results of FU challenge of 22L infected GTneo cells (6A) and Ch (6B) scrapie infected GTneo cells. GTneo cells after challenge with mock infected cells (−) show equivalent high levels of PrP-res already present in these cells. After challenge of 22L infected cells with FU infected GT cells, the pattern and amount of PrP-res is unchanged, indicating no appreciable superinfection. No 13 kd band diagnostic of FU is detectable. In contrast massive superinfection by FU is obvious in Ch infected cells. The PrP-res is markedly increased, and the 13 kd band is strong (C-13). The marker for 20 kd is indicated.

In more detail, for the experiments new persistent infections of GTneo target cells were established by standard application of infected Ch and 22L scrapie shown in FIG. 6, brain homogenates, and it was verified that these GTneo cells continued to produce substantial amounts of pathologic PrP-res for >15 in vitro passages before challenging them with GT+FU cells. The 22L and Ch scrapie infected GTneo target cells were then challenged with FU+GT cells which exhibit the 13 kd band.

The results in FIGS. 6A and 6B show scrapie strains 22L and Ch had different capacities for interfering with FU superinfection. The same antibiotic selection protocol was used before performing PrP-res assays. FIG. 6A (PrP-res profiles for representative mock and FU challenges to target 22L+ GTneo cells) show PrP-res intensity and band pattern in the target 22L cells exposed to FU (22L(FU) were indistinguishable from the 22L cells that were not challenged. The lack of the FU linked 13 kd band further confirms that the PrP-res reflected only the resident 22L infection. The 13 kd PrP-res band also did not appear with further in vitro passages, indicating it was not covertly contaminating the target cells. The protection afforded by 22L scrapie against FU-C,JD agent superinfection was complete and reproducible, as no extra PrP-res was detectable in two additional repeat experiments.

In sharp contrast, as shown in FIG. 6B, Ch scrapie infection did not protect GTneo cells from FU superinfection. PrP-res accumulation in these FU challenged cells (Ch(FU) was considerably more intense than in Ch-GTneo cells that were not challenged, and consistent with the amount of pathologic protein that would be provoked by infection with both agents.

The 13 kd band diagnostic of positive FU superinfection was also present. These Ch(FU) results were replicated two additional times.

These data also prove that large amounts of PrP-res itself have no inhibitory effect on superinfection, and that two different TSE agents can replicate and maintain their identity in a monotypic culture.

Example 5

Effect of Direct Cell Contact in Co-Culture

Because co-culture infection was so rapid and reproducible, additional experiments were done to determine if agent transmission was facilitated by cell-to-cell contact, or was more efficient with cell-free extracellular particles. Direct cell-to-cell contacts for efficient agent transmission can be important in vivo, as in the transfer of infectious agent from follicular dendritic cells to transiting white blood cells.

Mouse bioassays of concentrated supernatants collected from both 22L and FU infected GT cells were 1,000 fold less infectious than the remaining whole washed cells (data not shown). In addition, direct cell-to-cell contact was prevented by using 0.4 u filters between donor and target cells to permit the transit of large viruses and aggregates, but not whole cells. As in the co-culture experiments above, equal numbers of healthy donor and target cells were planted, and exposure was allowed to progress for weeks rather than days. When cell-cell contact was prevented, target cells required more in vitro passages to achieve production of PrP-res and target cells continually exposed to donor cells did not always become positive (data not shown), as would be predicted from the results above.

The invention claimed is:

1. A co-culture comprising at least one first cell line stably infected with a first mammalian TSE agent and at least one second cell line stably infected with a second mammalian TSE agent, or a tissue infected with said second mammalian TSE agent wherein said second TSE agent is more virulent than said first TSE agent.

2. The co-culture of claim 1, wherein said first cell line has been modified to be resistant to a mammalian antibiotic.

3. The co-culture of claim 2, wherein said antibiotic is neomycin.

4. A method to identify a candidate TSE agent for use in interfering with infection by a TSE agent which method comprises
    providing the co-culture of claim 1 and assessing the level of infection of the first cell line which is the target cell line by the second TSE agent which is the challenge TSE agent.

5. The method of claim 4, wherein said target cell line has been modified to be resistant to a mammalian antibiotic.

6. The method of claim 5, wherein said antibiotic is neomycin.

7. The method of claim 5, wherein the co-culture is treated with an antibiotic prior to said assessing the level of infection.

8. The method of claim 4, wherein said assessing is performed by measuring the level of the PrP-res in the target cell line, wherein said PrP-res level in said target cell line is compared to the PrP-res level in a mock cell line not infected with candidate TSE agent which has been similarly contacted with said challenge cell line or tissue,
    whereby a reduction in the level of PrP-res in said target cell line as compared to said mock cell line identifies said candidate TSE agent as a candidate molecule for use in interfering with the TSE infection.

* * * * *